United States Patent [19]

Cherubim et al.

[11] 3,948,993

[45] Apr. 6, 1976

[54] PROCESS FOR PRODUCTION OF 3-HYDROXY-CYCLOHEXENE-2-ONES

[75] Inventors: Martin Cherubim, Rheinkamp-Eick; Faisal AboDagga, Rheinkamp-Utfort, both of Germany

[73] Assignee: Deutsche Texaco Aktiengesellschaft, Hamburg, Germany

[22] Filed: Mar. 4, 1974

[21] Appl. No.: 447,710

Related U.S. Application Data

[62] Division of Ser. No. 284,190, Aug. 28, 1972, abandoned.

[52] U.S. Cl............ 260/586 C; 260/464; 260/465.1; 260/563 R; 260/621 R
[51] Int. Cl.²......................................... C07C 49/48
[58] Field of Search............. 260/464, 563 R, 586 C

[56] References Cited
UNITED STATES PATENTS

| | | | |
|---|---|---|---|
| 2,311,183 | 2/1943 | Bruson | 260/464 X |
| 2,394,962 | 2/1946 | Bruson | 260/464 X |
| 2,403,570 | 7/1946 | Wrest | 260/464 X |
| 2,437,906 | 3/1948 | Bruson et al. | 260/464 X |
| 3,759,973 | 9/1973 | Cherubim | 260/464 |

OTHER PUBLICATIONS

Favorskaya, et al., "Chem. Abstracts," 71;101666t(1969),

*Primary Examiner*—Norman Morgenstern
*Attorney, Agent, or Firm*—T. H. Whaley; C. G. Ries

[57] ABSTRACT

Substituted cyclohexene-2-ones are prepared by reacting a cyanoethylated ketone, such as 1,1,1-tri-beta-cyanoethyl acetone, in a polar solvent, e.g., methanol or water, in the presence of a catalyst. The compounds formed are useful in the production of cyclic amino acids, esters, hydroxy acids, as modifiers and as hardeners for phenolic and epoxide resins and as additives for lubricating oils.

2 Claims, No Drawings

PROCESS FOR PRODUCTION OF 3-HYDROXY-CYCLOHEXENE-2-ONES

This is a division of application Ser. No. 284,190, filed Aug. 28, 1972, now abandoned.

The present invention relates to a process for producing substitued cyclohexene-2-ones. More particularly, it relates to the production of substituted 3-amino-cyclohexene-(2)-ones and 3-hydroxy-cyclohexene-(2)-ones.

It is known that the presence of basic catalysts such as pyridine, quarternary ammonium hydroxide compounds or alkali allows reactive $CH_2$ groups to be added to activated C,C double bonds.

This addition, known as Michael's addition, has been employed also for the cyanoethylation of ketones; see, for example, U.S. Pat. No. 2,386,736. For the production of alpha-monocyanoethylated ketones it is also possible to react ketones with acrylonitrile in the presence of primary amines or the salts thereof in a pH range of from 5 to 12, as described in U.S. Pat. No. 2,850,519. By subsequent alkaline or acidic saponification of the nitrile groups of these cyanoethylated ketones the latter may be converted to their corresponding carboxylic acids or derivatives thereof.

In United States patent application Ser. No. 120,728 filed Mar. 3, 1971 there is disclosed a method of reacting diethylketone with acrylonitrile in the presence of a basic catalyst and suitable solvents to form cyclic ketones.

One object of this invention is to provide a simple process for the production of substituted cyclohexene-2-ones. It is another object of the invention to provide a process for producing 3-amino-cyclohexene-2-ones and 3-hydroxy-cyclohexene-2-ones substituted in 2-position and/or 6-position. It is a further object of the invention to provide a process for producing such substituted cyclohexene-2-ones in high yields with little concomitant formation of by-products.

The process of this invention for the production of substituted cyclohexene-2-ones comprises reacting a cyanoethylated ketone of the structural formula:

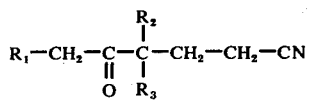

wherein $R_1$ is selected from the group consisting of hydrogen or alkyl having from 1 to 5, preferably from 1 to 3, carbon atoms and $R_2$ and $R_3$ are independently selected from the group consisting of hydrogen, alkyl having from 1 to 5, preferably from 1 to 3, carbon atoms or beta-cyanoethyl, in a polar solvent in the presence of a catalyst at a temperature ranging between about 20° to about 150°C.

Surprisingly, it has been found that the reaction of cyanoethylated aliphatic ketones to form cyclic ketones advantageously is conducted under reflux conditions.

The direct conversion of cyanoethylated ketones into cyclic compounds is advantageous in that purified cyanoethylated compounds may be used directly as starting materials and the amount of by-products occuring is substantially reduced. Additionally, this procedure permits the production of cyclic hexene-ones, which cannot be produced from ketones and acrylonitrile without isolating the cyanoethylated ketones.

In a particular embodiment of the invention, the reaction is conducted in the presence of a basic catalyst, resulting in the formation of 3-amino-cyclohexene-2-ones. In this embodiment, 1000 grams to 7000 grams, preferably 1500 to 6000 grams, of a polar solvent per mole of ketone and from 0.005 to 0.5 mole of basic catalyst are used. The most convenient reaction temperature is between 60° and 150°C. The preferred solvents include primary, secondary and tertiary alcohols boiling between 60° and 150°C, e.g., methanol, ethanol, and tert.-butanol. They may be used either individually or in combination with each other. Other solvents which are suitable for the process of the invention include aliphatic and cyclic ethers, e.g., tetrahydrofuran and dioxane, polar aliphatic and aromatic hydrocarbon derivatives and mixtures thereof, isopropanol, n-butanol, and sec.-butanol. Suitable catalysts include basic compounds such as hydroxides, alcoholates or other basic-reacting compounds in amount of from 0.005 to 0.5 mole per mole of cyanoethylated ketone.

The most favorable results are obtained when the catalyst is employed in an amount of from 0.02 to 0.2 mole per mole of the cyanoethylated ketone. Particularly suitable catalysts include alkali metal hydroxides such as sodium hydroxide or potassium hydroxide, alkaline earth hydroxides such as magnesium hydroxide, alkali metal alcoholates such as sodium propylate or potassium butylate and alkaline earth alcoholates such as calcium butylate. As distinct from the production of the cyclic products from the ketones and acrylonitrile, the alcoholates of primary and secondary alcohols may also be used in the process of the invention.

Advantageously, the reaction is conducted for a period of from 0.1 to 50 hours at a temperature below 150°C. If alcohols such as methanol, ethanol, propanol or butanol are used as solvent, the temperatures suitably range from about 60° to about 150°C.

The compounds prepared according to the invention may be used as intermediate products for organic syntheses, e.g., for the production of cyclic amino acids, esters, hydroxy acids and epoxide compounds, as raw materials for plastics for the production of polyamides, alkyl resins and ketonic resins as well as as modifiers and hardeners for phenolic and epoxide resins, and also as lubricating oil additives and raw materials for detergents.

In another preferred embodiment of the invention, the reaction is conducted in the presence of an acidic catalyst. The starting materials are cyanoethylated ketones of the afore-mentioned structural formula in which $R_1$ and $R_2$ are independently selected from the group consisting hydrogen or alkyl groups having from 1 to 5, preferably from 1 to 3, carbon atoms, and $R_3$ is hydrogen and the product obtained is a 2,6-dialkyl-3-hydroxy-cyclohexene-2-one. The polar solvent used is water. About 30 to 300 grams of water and from about 0.05 to about 2.0 moles of mineral acid as catalyst, based on one mole of ketone, are employed.

Suitable strong mineral acids for use in this process include, for example, phosphoric acid, hydrochloric acid and especially sulfuric acid. The reaction may be conducted in such a manner that the mono-cyanoethylated ketone is dissolved in water and the strong mineral acid is added dropwise. Preferably, the reaction temperature will range from about 50° to about 150°C. The reaction can be conducted over a period of from about 0.1 to 10 hours or more. Reaction times of from about 0.1 to about 1 hour are preferred.

The 3-hydroxy-cyclohexene-ones prepared according to the invention may be used as intermediate products for organic syntheses, particularly for the preparation of resorcinol derivatives, e.g., 2,6-dialkylresorcinol of the general formula:

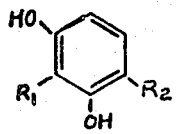

Such resorcinol derivatives may be used as starting materials for the production of phenolic resins and epoxide resins or as oxidation inhibitors and also as modifiers and hardeners. They are also suitable antioxidants for lubricating oils, elastomers and plastomers, they may be used as additives and are efficient bactericides. The resorcinol derivatives may be produced from the dialkyl-3-hydroxy-cyclohexenones by standard processes using aromatization.

The composition and the structure of the compounds prepared according to the invention were ascertained by carbon-hydrogen-nitrogen analysis, proof of functional groups, by chemical analyses, UV-, IR-, NMR-, and mass spectrophotometry as well as by determination of the molecular weight.

The invention is further illustrated by the following examples which are to be considered not limitative:

EXAMPLE 1

3-amino-6,6-(di-beta-cyanoethyl)-cyclohexene-(2)-one. Thirty grams of 1,1,1-tri-beta-cyanoethyl-acetone (0.138 mole) were heated at reflux in the presence of 600 ml of tert.-butanol and 15 ml. of a 10 percent KOH solution for 48 hours. After cooling, 150 ml of water were admixed, and the mixture was neutralized with diluted hydrochloric acid. The aqueous solution was extracted several times with chloroform, the extract dried with sodium sulfate and then concentrated in a rotary evaporator. The crystals were recrystallized from ethanol. Yield: 24.4 grams = 88 percent of theory of 3-amino-6,6-(di-beta-cyanoethyl)-cyclohexene-(2)-one. The melting point was 214° to 215°C.

CHN ANALYSIS

|  | C | H | N | molec. weight |
|---|---|---|---|---|
| Calculated | 66.3 | 6.96 | 19.35 | 217 |
| Found | 66.5 | 6.9 | 19.4 | 215 |

EXAMPLE 2

3-amino-6-methyl-6-(beta-cyanoethyl)-cyclohexene-(2)-one. Fifty grams of 2,2-di-(beta-cyanoethyl)-butanone-3, corresponding to 0.281 mole, were heated at reflux for 40 hours in the presence of 1.4 kg. of tert.-butanol and 25 ml of a 10 percent KOH solution. After cooling, 300 ml of water were added, and the mixture was neutralized with diluted hydrochloric acid. The aqueous solution was extracted several times with chloroform (about 3.5 l), the extract concentrated in the rotary evaporator, and the crystals obtained were recrystallized from ethanol. 45 grams of pure 3-amino-6-methyl-6-(beta-cyanoethyl)-cyclohexene-(2)-one, corresponding to 90 percent of theory, were obtained. Melting point: 158°C.

CHN ANALYSIS

|  | C | H | N | molec. weight |
|---|---|---|---|---|
| Calculated | 67.4 | 7.92 | 15.72 | 178 |
| Found | 67.6 | 7.9 | 15.7 | 182 |

EXAMPLE 3

2,6-dimethyl-3-amino-6-(beta-cyanoethyl)-cyclohexene-(2)-one. Twelve grams of 2,2-di-(beta-cyanoethyl)-pentanone-3, corresponding to 0.0562 mole, were heated at reflux for 20 hours in the presence of 100 ml of ethanol and 10 ml of a 10 percent KOH solution. After cooling, 100 ml of water were added, and the mixture was neutralized with hydrochloric acid. The aqueous solution was extracted with chloroform and dried with sodium sulfate following which the solvent was removed in the rotary evaporator. The crystals were recrystallized from methanol. 9.2 grams of 2,6-dimethyl-3-amino-6-(beta-cyanoethyl)-cyclohexene-(2)-one, corresponding to 80 percent of theory, were obtained. The melting point was 156°C.

CHN ANALYSIS

|  | C | H | N | molec. weight |
|---|---|---|---|---|
| Calculated | 68.72 | 8.39 | 14.54 | 192 |
| Found | 68.7 | 8.6 | 14.8 | 188 |

From the IR trace and the NMR spectrophotometric analyses, it was shown that the product was identical with the product known in the literature.

EXAMPLE 4

2,6-dimethyl-3-amino-cyclohexene-(2)-one. One hundred grams of 2-mono-(beta-cyanoethyl)-pentanone-3, corresponding to 0.72 mole, were heated at reflux for 24 hours in 3,000 grams of tert.-butanol and 50 ml of a 10 percent KOH solution. After addition of 750 ml of water, the reaction mixture was acidified with concentrated hydrochloric acid to a pH value of 5. Then, the reaction mixture was extracted several times with chloroform (2 liters) and the chloroform extract dried with sodium sulfate. The solvents were removed in a rotary evaporator.

Residue = 92 grams (raw yield) of 2,6-dimethyl-3-amino-cyclohexene-(2)-one = 92 percent of theory Melting point: between 75° and 80°C.

CHN ANALYSIS

|  | C | H | N | molec. weight |
|---|---|---|---|---|
| Calculated | 69.03 | 9.41 | 10.07 | 139.2 |
| Found | — | 9.4 | 9.5 | 140 |

EXAMPLE 5

2,6-dimethyl-3-hydroxy-cyclohexene-(2)-one. Sixty-four grams of 2-mono-(beta-cyanoethyl)-pentanone-3 (0.46 mole) were charged to a reactor together with 36 grams of water, and within five minutes 70.5 ml of concentrated sulfuric acid was added dropwise during which time the temperature rose to 130°C. The mixture was then heated at reflux for additional five minutes after which the mixture was poured into 600 ml of ice water, resulting in the separation of crystals which were filtered by suction and recrystallized from water (54 grams of 2,6-dimethyl-3-hydroxy-cyclohexene-(2)-one = 83 percent of theory). The melting point was between 115° and 117°C. The crystals were sensitive to humidity of the air.

CHN ANALYSIS

|  | C | H | molec. weight |
|---|---|---|---|
| Calculated | 68.54 | 8.63 | 140 |
| Found | 68.9 | 8.5 | 145 |

EXAMPLE 6

2,6-dimethylresorcinol 112.1 grams of 2,6-dimethyl-3-hydroxy-cyclohexene-(2)-one (0.8 mole) were heated at reflux in a 4-liter flask with 1682 ml of acetic acid anhydride and 78.6 grams of concentrated sulfuric acid under nitrogen and with mixing. During this operation the color of the mixture turned black. Subsequently, 1350 ml of the solution were distilled off. After cooling, the reaction mixture was poured into about 2 l of ice water and then extracted several times with ether.

Following removal of the solvent, the residue was heated at reflux with 700 ml of 18 percent hydrochloric acid for about 3 hours, followed by extraction with ether. The ether phase was then dried with calcium chloride and concentrated in a rotary evaporator. Sublimation of the residue gave 77 grams of 2,6-dimethylresorcinol, corresponding to 69.8 percent of theory. Melting point: 102° to 104°C.

CHN ANALYSIS

|  | C | H | molec. weight |
|---|---|---|---|
| Calculated | 69.54 | 7.30 | 138.16 |
| Found | 69.2 | 7.2 | 143 |

What is claimed is:

1. The process for the production of 3-hydroxy-cyclohexene-2-ones comprising reacting at a temperature of about 50° to about 150°C a cyanoethylated ketone of the formula:

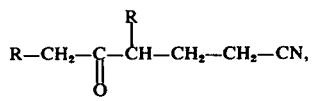

wherein R is selected from the group consisting of hydrogen and $CH_3$, in water and in the presence of a strong mineral acid, and wherein the said water is employed in an amount of from about 30 to about 300 grams per mole of ketone and wherein about 0.05 to 2.0 moles of mineral acid is employed per mole of ketone.

2. The process of claim 1 wherein the said mineral acid is selected from the group consisting of sulfuric acid and phosphoric acid.

* * * * *